United States Patent [19]

Carr et al.

[11] Patent Number: 5,081,305

[45] Date of Patent: Jan. 14, 1992

[54] PROCESS FOR THE PREPARATION OF BIS(AMINOPROPOXY)ALKANES

[75] Inventors: Richard V. C. Carr, Allentown; Steven M. Galaton, Doylestown; Thomas A. Johnson, Orefield; Thomas A. Albanese, Allentown, all of Pa.

[73] Assignee: Air Products and Chemicals, Inc., Allentown, Pa.

[21] Appl. No.: 257,479

[22] Filed: Oct. 13, 1988

[51] Int. Cl.⁵ .................. C07C 213/00; C07C 213/02
[52] U.S. Cl. ..................................... 564/490; 564/491; 558/450
[58] Field of Search ................. 564/490, 491; 558/450

[56] References Cited

U.S. PATENT DOCUMENTS

| | | | |
|---|---|---|---|
| 3,799,986 | 3/1974 | Poppelsdorf | 260/584 B |
| 3,957,848 | 5/1976 | Reedy et al. | 558/450 |
| 4,313,004 | 1/1982 | Kluger et al. | 564/491 |

Primary Examiner—Mukund J. Shah
Assistant Examiner—Philip I. Datlow
Attorney, Agent, or Firm—Russell L. Brewer; James C. Simmons; William F. Marsh

[57] ABSTRACT

This invention relates to a process for the separation of acrylonitrile used in the cyanoethylation of glycols to produce a bis(cyanoethylated) aliphatic glycol from the resulting glycol which is then reduced with hydrogen to produce the corresponding bis(aminopropoxy) alkane. In this process, acrylonitrile or methacrylonitrile is reacted with an aliphatic glycol in stoichiometric excess and the acrylonitrile removed from the cyanoethylated glycol by reaction with aliphatic primary or secondary alcohol prior to effecting the hydrogenation of the cyanoethylated aliphatic glycol in the presence of the acrylonitrile-amine reaction product. The reaction product then can be separated by conventional techniques such as distillation.

8 Claims, No Drawings

PROCESS FOR THE PREPARATION OF BIS(AMINOPROPOXY)ALKANES

TECHNICAL FIELD

This invention relates to a process for producing a cyanoethylated glycol by the reaction of acrylonitrile and an aliphatic glycol which is subsequently hydrogenated to form the corresponding bis(aminopropyl)aliphatic glycol or bis(aminoproxy)alkanes.

BACKGROUND OF THE INVENTION

U.S. Pat. No. 4,313,004 discloses a process for producing bis(aminopropyl)aliphatic glycols through a two step process comprising a first step of reacting acrylonitrile with an aliphatic glycol and then reducing the nitrile group by contacting the cyanoglycol with hydrogen in the presence of a hydrogenation catalyst. In this patent it is reported that various side reactions occur during the hydrogenation step and the extent of by-product formation is increased where residual acrylonitrile is present. For example, cyanoalkylated glycols may undergo cleavage to form undesired glycols, amino alcohols, polyamines and impurities or the acrylonitrile may react with the amine generated in the reduction, thereby contaminating the reaction product and presenting a separation problem.

U.S. Pat. No. 3,799,986 discloses a process for preparing amines by reacting an olefinic nitrile, such as acrylonitrile, with various polyhydroxy compounds followed by hydrogenation. In this process the olefinic nitrile is reacted with the polyhydroxy compound typically in stoichiometric proportions although excess of either can be utilized. After the condensation is completed, the olefinic nitrile is removed under reduced pressure. The patentees point out that it is sometimes difficult to remove the olefinic nitrile because of a tendency to polymerize and the polymerized nitrile impurity in the cyanoalkylated product may poison the hydrogenation catalyst during the hydrogenation step. In general the polymerized nitrile is removed by contacting the reaction mixture with solvents selective for the cyanoalkylated polyhydric alcohol reaction product such as saturated aliphatic and cycloaliphatic hydrocarbons. The hydrogenation then is carried out after removal of hydrocarbon solvent, typically in the presence of a tertiary amine or anhydrous ammonia. Ammonia and tertiary amine tend to minimize cleavage of the cyanoalkylated product during hydrogenation to the amine.

SUMMARY OF THE INSTANT INVENTION

This invention relates to an improvement in a process for preparing bis(aminoalkoxy)alkanes wherein acrylonitrile or methacrylonitrile is reacted with an aliphatic glycol and the resulting cyanoethylated glycol reduced to the corresponding amine by contacting the cyanoethylated glycol with hydrogen in the presence of a hydrogenation catalyst. The improvement resides first in the cyanoethylation stage wherein the acrylonitrile or methacrylonitrile is present in substantial stoichiometric excess, i.e., at least 100% stoichiometric excess to form the corresponding cyanoethylated glycol. After the initial cyanoethylation reaction, the reaction product is contacted with a primary or secondary aliphatic alcohol for reaction with the remaining acrylonitrile or methacrylonitrile and then said hydrogenation is accomplished by contacting the reaction mixture including, the reaction product of acrylonitrile or methacrylonitrile and aliphatic primary and/or secondary alcohol, with hydrogen to form the bis(aminoproxy)alkane.

There are significant advantages resulting from the improvement in the process, these are:

an ability to minimize byproduct formation caused by polymerization of acrylonitrile;

an ability to eliminate many of the separation problems caused by the generation of byproducts having boiling points similar to the amine formed in the reaction; and an ability to minimize by-product formation caused by reaction of acrylonitrile or methacrylonitrile with the hydrogenated cyanoethylated glycol.

DETAILED DESCRIPTION OF THE INVENTION

It is customary in the production of bis(cyanoethyl)-glycols to carry out the reaction under conditions that cyanoethylation is achieved at both of the hydroxyl group sites in the aliphatic glycol. Monocyanoethylation will result in the formation of a cyanoethoxy alkanol and when the cyano group is ultimately reduced, the resulting aminoalkanol is a chain terminator for polymer applications.

In accordance with this reaction, the aliphatic glycol is one generally having from about 2 to 20 carbon atoms and representative aliphatic glycols include ethylene glycol, propylene glycol, butylene glycol, etc.; and aliphatic ether glycols such as diethylene glycol, dipropylene glycol, dibutylene glycol and alkylene oxide derivatives of the aliphatic alcohols, e.g., of the ethylene glycol, propylene glycol, and butylene glycol. Such aliphatic glycols are widely used in the production of amines.

In the practice of this process, a stoichiometric excess of acrylonitrile or methacrylonitrile is used vis-a-vis the aliphatic glycol to insure that cyanoethylation of each hydroxy group in the aliphatic glycol is achieved. As previously mentioned, it is imperative that substantially all of the hydroxy groups be converted to the cyanoethylated derivative because a hydroxy group in the final product results in the formation of a product which may act as a chain stopper in some end use applications. For purposes of this process at least 117% acrylonitrile or methacrylonitrile of that stoichiometrically required for the conversion of all the hydroxy groups in the aliphatic glycol to the cyanoalkylated product is used, preferably at least 125%. As an upper limit, approximately 150% of the stoichiometric excess is suggested. Any level above this amount generally affords no significant advantages and requires removal of the acrylonitrile prior to hydrogenation. Temperatures of reaction typically range from 30°-70° C.

In contrast to prior art processes, which generally involved neutralization of the cyanoethylated reaction product to prevent reversal of the reaction during the separation process, this process converts the residual acrylonitrile or methacrylonitrile into a separable amine. Absent neutralization in the prior art, the cyanoethylated derivative sometimes cleaved at the ether oxygen reversing the reaction and generating the aliphatic glycol and olefinic nitrile. In the practice of this process an aliphatic primary or secondary alcohol having from 1 to 6 carbon atoms is added to the reaction product resulting from the reaction of acrylonitrile or methacrylonitrile and aliphatic glycol. These primary and secondary alcohols react with the excess acrylonitrile or methacrylonitrile to produce secondary and tertiary alkoxy derivatives. Examples of alcohols suited for reaction with acrylonitrile include methanol, ethanol, propanol, butanol, isobutanol, isopropanol, pentanol and so forth.

The reaction of residual acrylonitrile remaining after cyanoethylation of the aliphatic glycol with the alcohol can be carried out at a temperature of from about 0° to 50° C. at a pressure of from 1 to 4 atm°. In a preferred practice the reaction is carried out at modest temperatures to prevent reversal of the cyanoethylated aliphatic glycol to its original reactant, i.e., acrylonitrile or methacrylonitrile and aliphatic glycol.

After substantially all of the acrylonitrile or methacrylonitrile is reacted with the aliphatic alcohol, the hydrogenation of the cyanoethylated aliphatic glycol can be effected without separation of the reaction products. Hydrogenation is carried out in conventional manner, e.g., by contacting the cyanoethylated aliphatic glycol with hydrogen in the presence of a hydrogenation catalyst under hydrogenation conditions. Exemplary hydrogenation catalysts include Raney nickel, palladium, platinum, ruthenium, rhodium, and cobalt. Often ammonia is charged to the reaction zone to maintain high yield of the amino glycols and other derivatives.

The hydrogenation of the cyanoethylated derivative of the polyhydric alcohol may be carried out in the presence or absence of solvent. However, typically a solvent is used as it often enhances hydrogenation conditions. Examples of solvents include aliphatic alcohols such as methanol, ethanol, isopropanol or saturated hydrocarbons having from 5-12 carbon atoms such as hexane, cyclohexane, heptane, decane, etc. Temperatures of from 50° to 120° C. at hydrogenation pressures of 500 to 2,000 psig are used to carry out the reaction. Further details are set forth in U.S. Pat. No. 4,313,004 and the subject matter of that patent, including the procedures for hydrogenation described in the background portion of the patent, is incorporated by reference.

After hydrogenation of the cyanoethylated aliphatic glycol, the reaction product may then be separated. In contrast to the prior art, the boiling point and aliphatic primary and secondary alkoxy derivatives of acrylonitrile are substantially different from that of the bis-(aminopropxy)alkane resulting from the hydrogenation of the cyanoalkylated aliphatic glycol. Therefore, simple separation may be achieved through distillation.

The following examples are provided illustrate preferred embodiments and invention.

EXAMPLE 1

Preparation of bis(2-cyanoethoxy)ethane

Into a 1 liter, 3-necked round-bottom flask equipped with a thermometer, pressure-equalizing dropping funnel, reflux condenser and magnetic stir bar was placed 186 g (3.0 moles) of ethylene glycol and 1 g of anhydrous lithium hydroxide. The solution was warmed to 50° C. and then with agitation 397.5 g (7.5 moles) of acrylonitrile were added dropwise over 90 min. while maintaining the temperature between 50° and 60° C. Following addition of the acrylonitrile, the reaction mixture was stirred an additional 90 min. at 50° C. and then cooled and transferred to a 1 liter stirred autoclave.

At this time it was concluded cyanoethylation was complete.

EXAMPLE 2

Preparation of bis(2-cyanoethoxy)ethane/3-methoxypropionitrile mixture

As in Example 1, bis(2-cyanoethoxy)ethane was prepared by the addition of 623 g (11.73 moles) of acrylonitrile to 310 g (5.0 moles) of ethylene glycol containing 1.0 g of anhydrous lithium hydroxide at 55°-60° C. over a period of 90 min. The reaction was permitted to stir an additional 2 hr at 50° C. The reaction contents were cooled to 25° C. and 88.0 g (2.75 moles) of methanol was added over a period of 1 hr while maintaining the temperature between 25°-30° C. The mixture was allowed to stir an additional 12 hr at room temperature. Analysis by NMR revealed the crude product mixture to be 79.7 wt % of bis(2-cyanoethoxy)ethane, 17.4 wt % methoxypropionitrile, 1.78 wt % methanol, 0.72 wt % of 2-cyanoethoxyethanol, and 0.33 wt % acrylonitrile.

EXAMPLE 3

Preparation of bis(3-aminopropoxy)ethane/methoxypropylamine mixture

Into a 2 liter stirred autoclave was placed 60 g of Raney nickel 2400 and 120 g of anhydrous ammonia. A heel of 200 g of methanol was then pumped into the reactor and the reactor externally heated to 90° C. The pressure was raised to 850 psig with hydrogen. The crude product mixture of methoxypropionitrile (MOPN) and bis(cyanoethoxy)ethane from Example 4 was then pumped into the autoclave at a rate of 5.0 g/min until 999 g of the mixture had been admitted. During the addition the temperature was maintained at 90° C. and the pressure at 850 psig with hydrogen. Following the addition, hydrogen uptake ceased within 30 min. and the reaction was terminated. The contents of the autoclave were cooled and then filtered through Celite TM filtration aid. The filtrate was analyzed by GC and found to be comprised of 16.8 wt % 3-methoxypropylamine (MOPA), 77.0 wt % of bis(3-aminopropoxy)ethane, 0.89 wt % of 3-aminopropoxyethanol, 1.96 wt % of N-methoxypropyl-bis(3-amino-propoxy)ethane, 0.35 wt % of bis(3-methoxypropyl)amine and 3.0 wt % of bis(aminopropoxyethoxypropyl)amine.

EXAMPLE 4

Distillation of bis(3-aminopropoxy)ethane, and 3-methoxypropylamine

Distillation was performed on the material obtained in Example 3 following removal of methanol. Thus from 702 g of material was obtained 145.1 g of methoxypropylamine (61°-64° C. @ 160 torr), 97.8 g of an intermediate cut comprised of bis(3-aminopropoxy)ethane and 3-aminopropoxyethanol in a 10:1 ratio, 419.9 g of pure bis(3-aminoproxy)ethane (153°-157° C. @ 30 torr) leaving a pot residue of 93.6 g.

Examples 1-4 show that bis(cyanoethoxy)ethane is completely formed by the addition of excess acrylonitrile in a short time period. The excess acrylonitrile is removed by the addition of the aliphatic alcohol, methanol, in an amount stoichometric to the excess acrylonitrile. Hazardous distillation and recycle of unreacted acrylonitrile and 2-cyanoethoxy ethanol is avoided.

Other significant features shown by the examples show direct hydrogenation without decomposition and separation of the hydrogenated product from the reaction medium.

What is claimed is:

1. In a process for preparing a bis(aminopropyl)alkoxy glycol by reacting an aliphatic glycol with acrylonitrile or methacrylonitrile to produce a bis(cyanoethyl)alkoxy glycol and then hydrogenating the resulting bis(cyanoethyl)alkoxy glycol to produce the corresponding bis(aminopropyl)alkoxy glycol, the improvement which comprises:

effecting a cyanoethylation reaction between acrylonitrile or methacrylonitrile and said aliphatic glycol under conditions such that the acrylonitrile or methacrylonitrile is present in at least 117% of that stoichiometrically required for the cyanoethylation reaction and reacting said excess acrylonitrile or methacrylonitrile from the cyanoethylation reaction between said acrylonitrile or methacrylonitrile and aliphatic glycol with an aliphatic alcohol selected from the group consisting of methanol, ethanol, propanol, isobutanol, isopropanol, and pentanol to form a cyanoethylated alcohol;

hydrogenating the mixture of bis(cyanoethyl)alkoxy glycol and cyanoethylated alcohol to form said bis(aminopropyl)alkoxy glycol and then, distilling the bis(aminopropyl)alkoxy glycol from the alkoxypropylamine.

2. The process of claim 1 wherein said aliphatic glycol has from 2-20 carbon atoms.

3. The process of claim 2 wherein said nitrile is acrylonitrile and said reaction with said aliphatic glycol is conducted at a temperature from 30° to 70° C.

4. The process of claim 3 wherein the acrylonitrile is present in an amount from 117-150% required for stoichiometric reaction with said glycol.

5. The process of claim 4 wherein said aliphatic glycol is ethylene glycol.

6. The process of claim 4 wherein said glycol is diethylene glycol.

7. The process of claim 4 wherein said alcohol is methanol.

8. The process of claim 5 wherein said alcohol is ethanol.

* * * * *